(12) United States Patent
Cook

(10) Patent No.: US 6,443,927 B1
(45) Date of Patent: Sep. 3, 2002

(54) NEEDLE ENCLOSING SAFETY CATHETER

(76) Inventor: Daniel J. Cook, 1167 Hillside Dr., Richmond Heights, MO (US) 63117

( * ) Notice: Subject to any disclaimer, the term of this patent is extended or adjusted under 35 U.S.C. 154(b) by 58 days.

(21) Appl. No.: 09/778,201

(22) Filed: Feb. 6, 2001

(51) Int. Cl.$^7$ .............................................. A61M 5/178
(52) U.S. Cl. ................... 604/110; 604/164.08
(58) Field of Search ............................ 604/164.08, 110, 604/163, 263

(56) References Cited

U.S. PATENT DOCUMENTS

| | | | | |
|---|---|---|---|---|
| 5,611,781 A | * | 3/1997 | Sircom et al. ............... | 604/263 |
| 6,221,047 B1 | * | 4/2001 | Greene et al. .......... | 604/164.08 |
| 6,322,537 B1 | * | 11/2001 | Chang ........................ | 604/110 |

* cited by examiner

Primary Examiner—Philippe Derakshani
(74) Attorney, Agent, or Firm—Gregory Upchurch; Ahaji Amos; Thompson Coburn, LLP

(57) ABSTRACT

A catheter and needle system includes a solid piercing needle, a catheter, and a needle tip enclosure, as well as a method of utilization. The solid needle reduces the possibility of transmitting infectious agents to a user otherwise resulting from accidental needle punctures. The system has two configurations, a first for inserting the assembly into a patient, and a second for withdrawing and disposing of the piercing needle. The catheter has means for receiving, delivering and viewing fluids at the insertion site. The needle and enclosure operate cooperatively to enable medical procedures to be conducted without hindrance, and to automatically cleanse and enclose the piercing portion of the needle upon withdrawal. The system also provides for the safe withdrawal of the needle without the need to disturb the catheter once it is inserted.

32 Claims, 2 Drawing Sheets

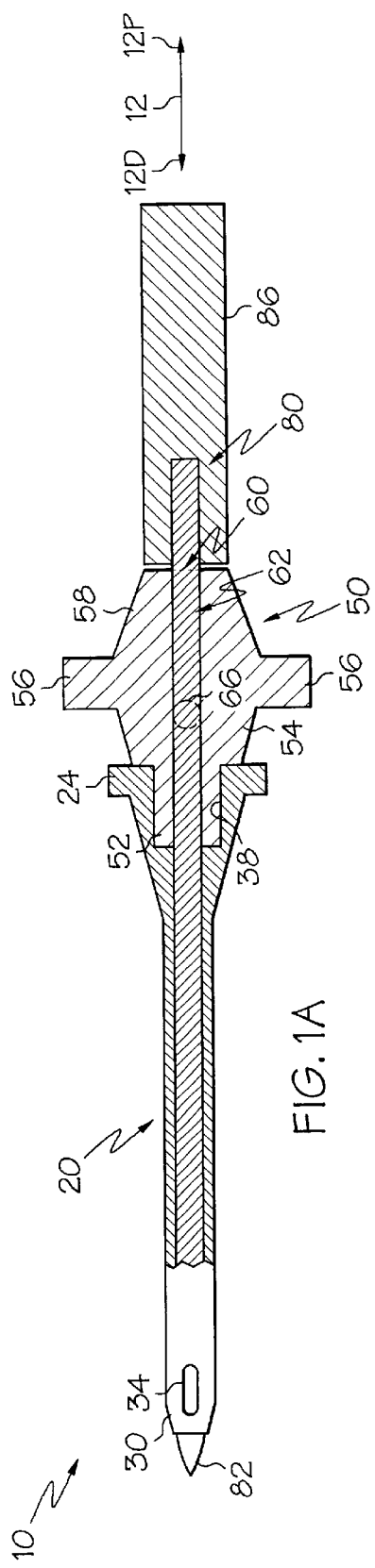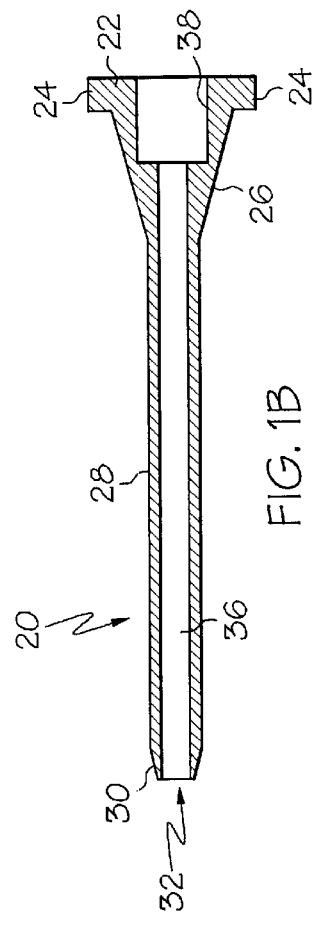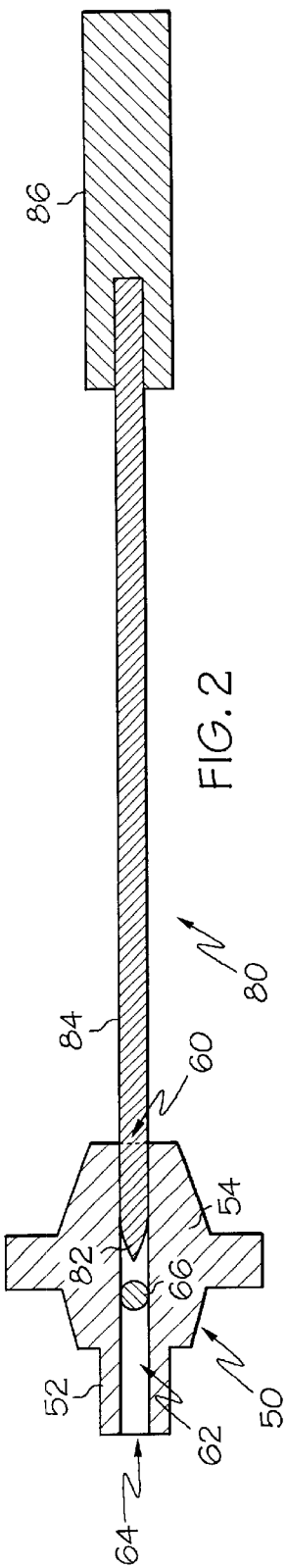

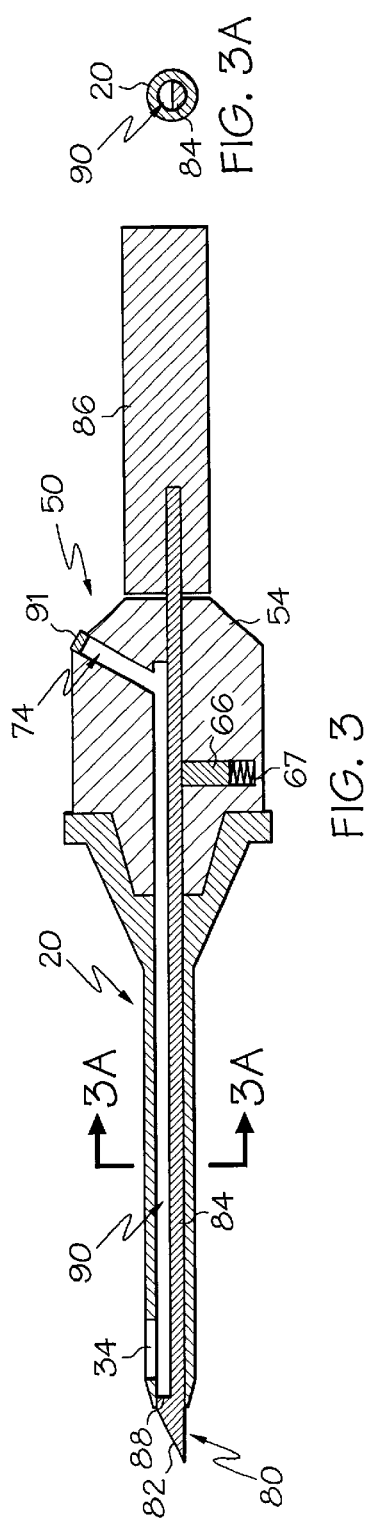
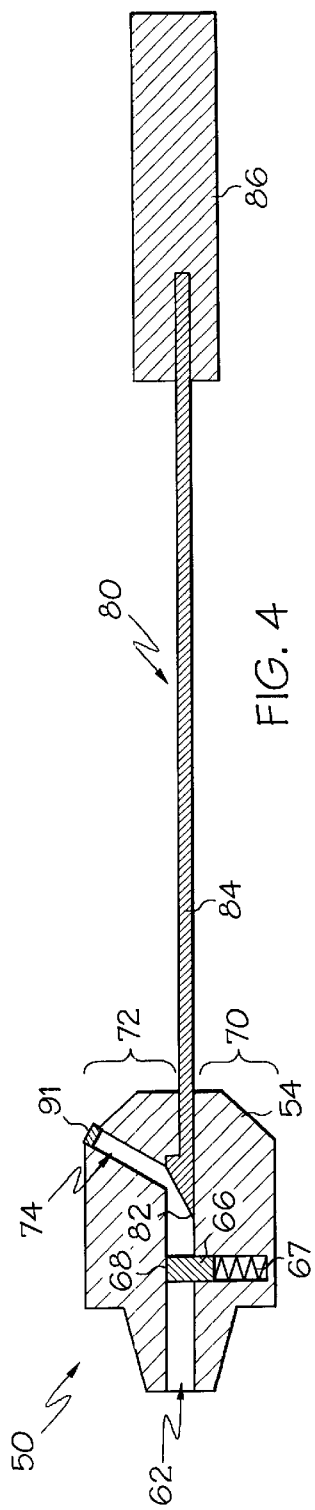
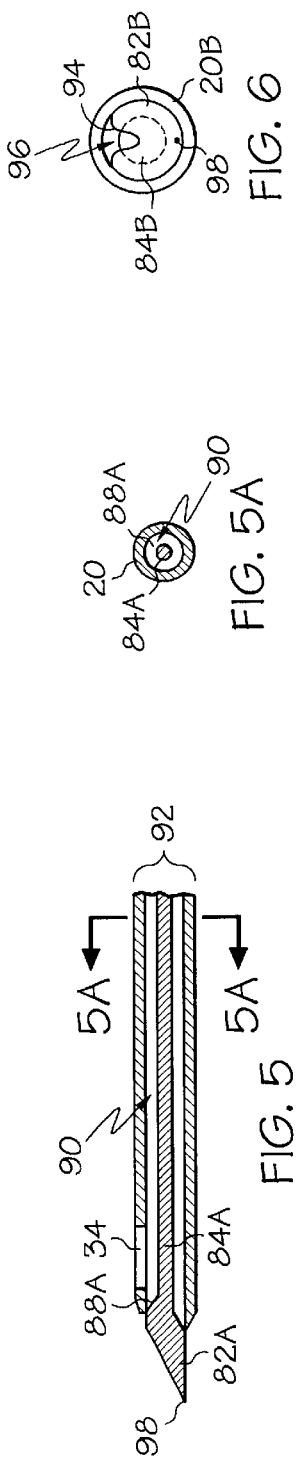
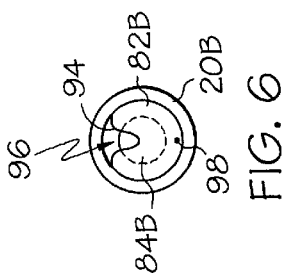

NEEDLE ENCLOSING SAFETY CATHETER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Numerous medical procedures involve the insertion of intravenous devices into patients with varying medical conditions. Among these medical conditions are a number of diseases that also present a risk of infection to the medical practitioner providing care. The insertion of intravenous devices generally requires the use of a sharp implement, which conventionally has been a hollow bore needle, for piercing the skin to allow insertion of a hollow catheter. The distal end of the catheter must be inserted into, but not through, a blood vessel. Normally, proper placement of the catheter is confirmed by visual observation of a "flash-back" of blood that passes through the hollow needle into a stationary flash chamber located at the proximal end of the catheter assembly, where it is visualized. Once the catheter has been inserted to the proper position within the blood vessel, the sharp implement needs to be withdrawn and properly discarded. The acts of withdrawal and disposal pose the greatest threat to the health of the practitioner, since the implement remains sharp enough to pierce skin and is potentially carrying an infectious agent. With the prior art designs, the hollow needle and flash chamber contain a rather large amount of potentially infectious blood, with the result that inadvertent skin puncture of the practitioner can lead to significant transference of infectious agent from the patient to the practioner.

A system for providing protection from the risk of infection during withdrawal and disposal of a piercing instrument must accommodate various operational constraints. A primary constraint is to minimize interference with the execution of the medical procedure prior to withdrawal and disposal. Accordingly, the system should minimize or eliminate additional steps and preferably should not significantly alter the steps performed without the system. Medical care often occurs in stressful and hurried situations and hence, ease of use is a second constraint. Preferably, the system should not compel the practitioner to carry out any but the most minimal actions to accomplish safe withdrawal and disposal. Additional constraints include cost and ease of construction, compatibility with existing equipment, and adaptability of use across variations in patients and insertion locations.

A very desirable benefit of such systems would be reduction in the risk of accidental infection. Risk of infection can be reduced by, inter alia, automatic operation, encapsulation of the piercing implement, and a reduction in the fluid and tissue volume associated with piercing instrument removal—since greater volume potentially increases the amount of the infectious agent present. Risk can also be reduced by quick operation. If the system is effective simultaneously with, or at least immediately subsequent to withdrawal, exposure of the piercing instrument is minimized, as is the risk of accidental infection.

Numerous approaches to providing a safer withdrawal and disposal system have been employed, though two general categories of systems predominate. One category of system deploys a secondary sheath between a needle and a catheter to envelope the needle upon withdrawal from the piercing site, prior to complete withdrawal of the secondary sheath and needle from the catheter. This category of system is relatively sizable and complex, yet still poses a risk of reemergence of the needle. Preventing reemergence may necessitate even more apparatus. Withdrawal is also generally associated with emission of a significant amount of body fluid with this category of system, among other adverse consequences. The second category of system involves affixing a point guard about the tip of the piercing instrument after withdrawal. This approach often requires substantial complexity and substantial additional actions to implement. What's more, with this second category of system, better execution of one desirable benefit, such as secure encapsulation of a piercing instrument, is often exchanged for a poorer execution of another desirable benefit, such as automatic operation.

As mentioned above, most prior approaches utilize a hollow needle (in fluid communication with a stationary flash chamber having a relatively large volume) for piercing. Hollow needle and flash chamber assemblies, however, present a risk of exposure to the body fluids they contain when the needle is withdrawn. In fact, research reveals that the risk of infection from a hollow needle is many times greater than that from a solid needle. This difference probably arises from the large reservoir of blood within the hollow needle and flash chamber assembly, that then becomes the source of inoculation when inadvertent needle stick injuries occur. Solid needles, on the other hand, have no such reservoir for inoculation. Moreover, when using a hollow needle with a catheter the user may receive an incorrect "flashback" signal. The "flashback" signal is the entry, or "flashing", of blood into a viewing chamber (called the flashback chamber) in the interior of the catheter and needle system. The flash occurs when a blood vessel is entered and blood can flow into the catheter interior. Hollow needles allow blood to flow into the catheter interior even if only the needle, but not the catheter, has entered the blood vessel. Hence, the user must guess to what degree it is necessary to further insert the needle and catheter, after observing the flashback, to ensure that the catheter is correctly inserted. A system providing greater certainty of correct catheter insertion is preferable.

SUMMARY OF THE INVENTION

The objectives of the present invention include:

The provision of an improved piercing system which entails a minimum of hindrance to the optimum execution of a medical procedure.

The provision of an improved piercing system that requires minimum additional actions following the execution of a medical procedure such as the insertion of a catheter.

The provision of an improved piercing system that requires minimal alterations of the actions involved in the execution of a medical procedure such as the insertion of a catheter.

The provision of an improved piercing system with ease of use sufficient to curtail any additional demands on the medical practitioner's attention.

The provision of an improved piercing system that requires minimal additional actions by the medical practitioner to realize the improvement in safety.

The provision of an improved system and method for catheter insertion using a solid needle to reduce the possibility of infection transference.

The provision of an improved piercing system that is relatively inexpensive.

The provision of an improved piercing system of simplified construction.

The provision of an improved piercing system compatible with existing medical equipment.

The provision of an improved piercing system adaptable for use across variations in patients and piercing locations.

The provision of an improved piercing system that reduces the risk of accidental infection.

The provision of an improved piercing system that operates automatically.

The provision of an improved piercing system that completely encloses the penetrating elements of the piercing instrument.

The provision of an improved piercing system that reduces the amount of fluids and tissue which accompany withdrawal of the piercing instrument.

The provision of an improved piercing system that occurs sufficiently fast to be in effect simultaneously with or at least immediately after withdrawal of the piercing instrument.

The provision of an improved piercing system, comprised of a catheter and needle, that gives visual confirmation only when the catheter is correctly inserted, and not when just the needle is correctly inserted.

BRIEF DESCRIPTION OF THE DRAWINGS

FIG. 1A is a longitudinal partial cross-section top plan view of a first embodiment of the present invention in a first configuration.

FIG. 1B is a longitudinal cross-section top plan view of a catheter portion of the first embodiment of the present invention depicted in FIG. 1A.

FIG. 2 is a longitudinal partial cross-section top plan view of two parts of the first embodiment of the present invention in a second configuration.

FIG. 3 is a longitudinal cross-sectional elevation of the first embodiment of the present invention, in the configuration of FIG. 1A.

FIG. 3A is a cross-section view along line 3A—3A in FIG. 3 of a needle element of the first embodiment of the present invention.

FIG. 4 is a longitudinal cross-sectional elevation of the first embodiment of the present invention, in the second configuration shown in FIG. 2.

FIG. 5 is a longitudinal cross-sectional elevation similar to a portion of FIG. 3, illustrating a second embodiment of the present invention.

FIG. 5A is a cross-sectional view along line 5A—5A of portions of catheter and needle elements of the second embodiment of the present invention.

FIG. 6 is a view along the longitudinal axis 12 in the direction 12P of FIG. 1A, of a catheter and needle tip of a third embodiment of the present invention.

Similar reference characters indicate similar parts throughout the several views of the drawings.

DETAILED DESCRIPTION OF THE PREFERRED EMBODIMENT

In FIGS. 1A, 1B & 2–4 a first embodiment of a catheter and needle assembly 10 of the present invention is shown in two configurations. A first configuration for insertion of the catheter and needle assembly is depicted in FIGS. 1A & 3. Two components of the catheter and needle assembly, in a second configuration for safe withdrawal and disposal following insertion, is depicted in FIGS. 2 & 4.

Referring now to FIG. 1A, a first embodiment of a needle tip enclosing catheter and needle assembly 10 in the first configuration is depicted in partial cross-section. The catheter and needle assembly has a longitudinal axis 12, with a proximal direction 12P and a distal direction 12D. Directions referred to hereafter as transverse are perpendicular to the longitudinal axis 12. It should be understood that in the FIGURES, the catheter and needle assemblies are depicted in straight linear configurations for purposes of clarity only. Depending upon the application, the catheter and needle assembly may have both flexible and inflexible portions. Accordingly, axis 12, though depicted as a straight line, may also be curvilinear in correspondence to the actual disposition of assembly 10 when in use. In a case of curvilinear disposition, directions 12P and 12D indicate relative directions along the longitudinal extent of the catheter and needle assembly. The direction 12P is along axis 12 pointing towards the proximal end of the assembly, and the direction 12D is along axis 12 pointing towards the distal end of the assembly.

FIG. 1B is a cross-section view of a catheter 20 employed in the first embodiment. Catheter 20 has a proximal base 22 with a plurality of flanges 24 that flare transversely. Base 22 adjoins a transitional section 26 which connects to a conduit 28. Conduit 28 terminates in a distal tip 30. An opening 32 is formed in distal tip 30.

Returning to FIG. 1A, catheter 20 is shown in relation to the other parts of the assembly 10 when in the first configuration for insertion into a blood vessel (not shown). An aperture 34 proximate tip 30 is in fluid communication with an interior passageway 36—seen in FIG. 1B—of catheter 20. A catheter hub 38 securely mates with a needle tip enclosure 50 at a distal enclosure adaptor 52. Enclosure 50 has an enclosure housing 54, which includes a plurality of intermediate side tabs 56. A proximal portion 58 of enclosure housing 54 has a proximal orifice 60 formed therein. Proximal orifice 60 is in fluid communication with a cavity 62. Cavity 62 runs longitudinally through enclosure housing 54 to a distal orifice 64.

Referring now to FIG. 2, a cross-section view of needle tip enclosure 50 is depicted in the second configuration, following successful insertion of catheter 20 into a blood vessel (not shown). Within the cavity 62 is a blocking member 66, seen end-on. When in the second configuration, the position of blocking member 66 obstructs movement through the cavity 62.

In FIG. 4, blocking member 66, forced by a spring 67 (or by any other conventional device or material), crosses cavity 62 and contacts an interior wall 68 of the enclosure housing 54. Housing 54 has first and second sides 70 and 72. In a proximal portion of side 72 is a vent 74 from the cavity 62.

Referring again to FIG. 2, a solid piercing needle 80 and enclosure 50 are depicted in the second configuration. The solid needle 80 has a distal tip 82 and a shaft 84 (shown to be semi-elliptical in cross-section—FIG. 3A), and is attached to a proximal control element 86. In FIG. 3, needle tip 82 is seen to have a proximal face 88 at the boundary between the tip 82 and the shaft 84.

In operation, assembly 10 is initially in the first configuration (shown in FIGS. 1A and 3) for inserting catheter 20 by piercing the skin with solid needle tip 82. In the first configuration, enclosure adaptor 52 is fully engaged in hub 38, needle 80 is at its farthest distal position in catheter 20 and needle enclosure 50, and needle tip 82 emerges from the distal opening 32 in readiness for piercing the skin of the patient. During insertion, needle control element 86 is flush against the enclosure 50 with needle shaft 84 passing throughout the enclosure cavity 62 and the catheter interior passageway 36. Within cavity 62, needle shaft 84 confines the blocking member 66 to a first position that is not obstructing cavity 62 as depicted in FIG. 3. Also in the first configuration, the proximal face 88 of needle tip 82 is disposed distally past aperture 34, to allow passage of bodily fluids through aperture 34 and into an open space 90 within interior passageway 36. The space 90 is the fraction of interior passageway 36 and cavity 62 not occupied by needle shaft 84. Vent 74 is closed by a well-known air permissible plug 91 that allows air to escape from housing 54 but prevents the escape of blood or other body fluids. At least a portion of housing 54 is preferably transparent to form a movable flashback chamber (space 90 and vent 74) which is visible to the user. When aperture 34 enters the blood vessel, blood flows along space 90 into housing 54 where it is visible to the user through the transparent portion (not depicted) of housing 54. In contrast to prior approaches, the flow of blood along space 90 does not occur immediately upon insertion of the needle 80 into a blood vessel. The prior approaches use hollow needles that allow blood flow through the hollow needle and into the catheter and into a hollow flash chamber in the proximal portion of the apparatus. These approaches allow the blood flow into the catheter and flash chamber even if the needle is inserted in the blood vessel, but the catheter is not. Hence, there is a degree of uncertainty as to whether the catheter is correctly inserted with the prior approaches. The solid needle 80, catheter 20, and aperture 34 of the present invention cooperate to allow blood flow into space 90 only once the catheter 20 is correctly inserted such that aperture 34 of catheter 20 has entered a blood vessel. This "flashback" of blood indicates proper placement of catheter 20. Inspection of the flash chamber allows the medical practitioner inserting the catheter and needle assembly 10 to visually determine if the assembly is correctly inserted, i.e., the catheter tip containing aperture 34 has entered the blood vessel.

After insertion of catheter 20, removal and disposal of needle 80 will follow. Once the catheter and needle assembly 10 is inserted into a blood vessel, needle enclosure 50 is moved distally along direction 12D (Fig. 1A) while simultaneously needle 80 is withdrawn proximally along direction 12P until needle tip 82 is completely within enclosure 50. This movement of enclosure or housing 50 distally relative to the proximal movement of needle 80 automatically disposes catheter 20 within the blood vessel. The transition to the second configuration is complete when needle tip 82 is locked within enclosure 50 by blocking member 66 crossing cavity 62. Needle 80 and enclosure 50 are usually then separated from catheter 20, which is left inserted in the blood vessel. Also the construction and operation of enclosure 50, as it moves proximally along direction 12P from configuration 1 (shown in FIGS. 1A and 3) to configuration 2 (shown in FIGS. 2 and 4), in cooperation with the construction of needle 80, automatically effects a cleansing and encapsulation of needle 80.

Beginning from the first configuration (FIGS. 1A, 3), withdrawal is initiated by movement of needle 80 in the proximal direction 12P relative to catheter 20 and enclosure 50. Proximal orifice 60 is constructed to fit closely to, while still allowing relatively unimpeded travel of, shaft 84. This close fit provides at least two functional benefits. The first benefit is the prevention of escape of needle tip 82 from enclosure 50 in the direction 12P, since the needle tip cross-section is too great to pass through proximal orifice 60. The second benefit, as a result of the close fit of proximal orifice 60 to shaft 84, is a wiping off of body fluids and tissue from shaft 84 as it passes through proximal orifice 60. This wiping reduces the medical practitioner's exposure to infectious agents along shaft 84 by limiting the emission of fluids and tissues that accompanies the withdrawal of needle 80. Once the needle tip 82 has left catheter 20, needle tip 82 enters cavity 62. As enclosure 50 moves distally and needle 80 simultaneously moves proximally, fluids in space 90 pass around tip 82 and remain within catheter 20 or exit into vent 74, as a result of the relatively loose fit between the body of catheter 20 and needle 80. Vent cap 91 prevents egress of fluids outside enclosure 50. This movement of fluids out of space 90 during the transition from configuration 1 to configuration 2 minimizes the total fluid held within enclosure 50 at the completion of catheter insertion. This in turn minimizes the volume of potential contaminants to which the practitioner is exposed.

Upon sufficient movement of the needle proximally into cavity 62, needle tip 82 passes blocking member 66, thereby releasing blocking member 66. Upon release, member 66 is moved by spring 67 (or other suitable flexible material or structure) to the position shown in FIG. 4 in which it blocks cavity 62, thereby trapping tip 82 in enclosure 50. Alternatively, the housing interior wall 68 may have a recess (not depicted) that the blocking member 66 fits into for a more secure closure of cavity 62. The presence of member 66 blocking cavity 62 is a barrier to the reemergence of needle tip 82. When positioned across cavity 62, blocking member 66 also tends to prevent passage of fluids and tissues from cavity 62 and vent 74 through distal orifice 64. Also during transition from configuration 1 to configuration 2 the total volume of blood contained within the flash chamber of enclosure 50 has been minimized and positioned distally away from the practitioner, thereby potentially decreasing the likelihood of exposure. The operation of enclosure 50 is automatic upon removal of the needle 80 and requires minimal additional or altered actions by the medical practitioner. The movement of catheter 20 into the blood vessel following catheter tip placement occurs automatically during proximal movement of enclosure 50 along needle 80. Once entirely removed, needle tip 82 is contained within enclosure 50, and needle 80 and enclosure 50 can be discarded without exposing the practitioner to contaminated needle tip 82.

Viewed in cross-section along line 3A—3A in FIG. 3, FIG. 3A shows how the spatial relationships of catheter 20 and needle shaft 84 provide the space 90. In alternate embodiments (not depicted), shaft 84 may occupy a lesser amount of the cross-sectional area of catheter 20. In these embodiments, the space 90 will be a greater fraction of the cross-sectional area of catheter 20, and space 90 may also extend around the sides or below needle shaft 84.

The transverse cross-section of catheter 20 and needle 80, as well as the form of the needle tip 82, can differ both in size and shape in various embodiments. Particular medical applications will preferentially utilize specific configurations, including both symmetrical and asymmetrical structures. The movable transparent flash chambers can also differ in size, shape and topography in various embodiments of the present invention when advantageous.

Referring now to FIGS. 5, a second embodiment of the present invention is partially depicted in cross-section. Significant modifications from the prior embodiment include: the form of a needle tip 82A, the relation of tip 82A to a shaft 84A, and the form of a proximal face 88A. The disposition of needle shaft 84A within space 90 is also altered, in part, due to the modified relation of tip 82A to shaft 84A. Needle shaft 84A having the option, as depicted, of a relatively lesser cross-sectional area than needle shaft 84 also contributes to its altered disposition within space 90. FIG. 5A shows both the transverse cross-section of needle shaft 84A within the space 90, and the proximal portion 88A of needle tip 82A. The axial position of needle shaft 84A is approximately centered in relation to the distal tip 82A. The embodiment depicted in FIGS. 5 & 5A is well suited for providing an alternative option in medical circumstances, such as pediatric care, where a catheter with a lesser width 92 is desirable.

Referring now to FIG. 6, a third embodiment of the present invention is depicted in an increased scale relative to FIG. 5. FIG. 6 shows an alternative needle tip 82B which is differentiated from needle tip 82A of FIGS. 5 & 5A by the presence of a needle groove 94. Needle groove 94 extends longitudinally through the tip 82B and may also extend along a portion of the length of a shaft 84B, partially seen through a gap 96 formed by the sides of groove 94 and a catheter 20B. Catheter 20B is identical to the catheter 20 of the previous embodiments except for a lack of aperture 34. Groove 94 is of sufficient depth to allow the flow of bodily fluids through gap 96 between the boundaries of groove 94 and catheter 20B, into the open space 90. As depicted, the radius of shaft 84B is greater than is the radius of tip 82B at the bottom of groove 94. Alternatively, the bottom of groove 94 may reach to a lesser depth (not depicted), such that the radius of tip 82B at the bottom of groove 94 is not less than the radius of the shaft 84B. An additional alternative embodiment (not depicted) would continue groove 94 along part or all of shaft 84B to further increase the space 90 available for blood flow. A distal point 98 of needle tip 82B is seen to be off-centered, relative to the longitudinal axis 12. The distal point 98 may also be arranged to one side or the other of groove 94 (not depicted) or centered (not depicted) relative to the longitudinal axis 12. These variations in the disposition of distal point 98 may also be optionally employed with any of the other embodiments of the present invention.

A variety of physical mechanisms can serve as the blocking member 66. Although only one example is depicted herein for illustrative purposes, numerous variations in the construction of the blocking member 66, variations in the means of biasing towards a blocking position, as well as variations in the means of effecting a blocking action upon needle withdrawal are within the scope of the present invention. The various applicable mechanisms are well known to those of skill in the art, and do not compromise elements essential to the present invention.

In view of the above, it will be seen that the various objects and features of the invention are achieved and other advantageous results obtained. The examples contained herein are merely illustrative and are not intended in a limiting sense.

What is claimed is:

1. A catheter and needle assembly comprising:
    a catheter having a body defining an interior passageway with a distal and a proximal opening,
    a solid needle having a shaft and a distal tip,
    a needle tip enclosure at the catheter's proximal opening, said enclosure containing a cavity therethrough;
    said needle shaft having a length sufficient to extend through the enclosure cavity and the catheter passageway so that said needle tip emerges at the catheter distal opening, said passageway and needle being cooperatively structured to provide a flow channel in the catheter passageway for bodily fluids; and
    said needle being of a size which permits it to be withdrawn from the catheter such that the needle tip enters the enclosure cavity through a distal orifice of the enclosure, said needle tip being shaped to prevent egress of the needle tip from the cavity through a proximal orifice, and said enclosure, upon passage of the needle tip into the cavity through the distal orifice, preventing reemergence of the needle tip from the distal orifice, thereby trapping the needle tip in the needle tip enclosure.

2. The catheter and needle assembly of claim 1 wherein at least a portion of the longitudinal extent of the catheter body is transparent for viewing said interior passageway.

3. The catheter and needle assembly of claim 1 wherein at least a portion of the needle tip enclosure is transparent for viewing said cavity.

4. The catheter and needle assembly of claim 1 wherein said flow channel is an open volume within the interior passageway that is unoccupied by the needle shaft.

5. The catheter and needle assembly of claim 1 wherein said flow channel is formed by a longitudinal groove in the needle.

6. The catheter and needle assembly of claim 1 wherein said catheter body has an aperture proximate the distal opening for entry of bodily fluids to the interior passageway.

7. The catheter and needle assembly of claim 1 wherein said needle tip is of a greater width in at least one direction transverse to its longitudinal extent than the width of the needle shaft in said transverse direction.

8. The catheter and needle assembly of claim 7 wherein said enclosure proximal orifice is of a lesser width than the maximum width of the needle tip in said one transverse direction.

9. The catheter and needle assembly of claim 1 further including a vent from the enclosure cavity.

10. The catheter and needle assembly of claim 1 wherein a transverse cross-section of the needle tip substantially corresponds to a transverse cross-section of the enclosure cavity.

11. The catheter and needle assembly of claim 1 wherein the transverse cross-section of the enclosure cavity substantially corresponds to the transverse cross-section of the catheter interior passageway.

12. The catheter and needle assembly of claim 1 wherein the enclosure cavity includes a blocking member that prevents reemergence of the needle tip by obstructing a portion of the enclosure cavity once the needle tip is sufficiently far into the enclosure cavity.

13. The catheter and needle assembly of claim 12 wherein the blocking member is biased towards the enclosure cavity, and removal of the needle from the vicinity of the blocking member allows the blocking member to move in response to the bias to obstruct a portion of the enclosure cavity.

14. The catheter and needle assembly of claim 12 wherein the obstructing of a portion of the enclosure cavity by the blocking member is selectively controllable.

15. The catheter and needle assembly of claim 12 wherein the blocking member is seated in a receiving indentation in an interior wall of the enclosure cavity when obstructing a portion of the enclosure cavity.

16. The catheter and needle assembly of claim 1 wherein said needle and enclosure with enclosed needle tip is detachable from said catheter.

17. A method of inserting a catheter and needle assembly comprising the steps of:

provifing a catheter and needle assembly which includes;
a catheter having a body defining an interior passageway with a distal and a proximal opening,
a solid needle having a shaft and a distal tip, a needle tip enclosure at the catheter's proximal opening, said enclosure containing a cavity therethrough;
said needle shaft having a length sufficient to extend through the enclosure cavity and the catheter passageway such that said needle tip emerges at the catheter distal opening when in a first configuration;
said passageway and needle being cooperatively structured to provide a flow channel for bodily fluids in the catheter passageway when in said first configuration;
said needle being of a size to permit withdrawal from the catheter such that the needle tip can enter the enclosure cavity through a distal orifice of the enclosure, said needle tip being shaped to prevent egress of the needle tip from the cavity through a proximal orifice of the enclosure, and said enclosure, upon passage of the needle tip into the cavity through the distal orifice, prevents reemergence of the needle tip from the distal orifice;
wherein said catheter and needle assembly is in a second configuration when said needle tip is withdrawn from the catheter into the enclosure and is prevented from reemergence;
disposing said catheter and needle assembly in said first configuration and inserting the catheter and needle assembly into a patient; and then
shifting said catheter and needle assembly, following insertion, from said first configuration into said second configuration.

18. The method according to claim 17 including the additional step of: detaching the needle and enclosure with enclosed needle tip from the catheter, which is left inserted.

19. A method of inserting a catheter and needle assembly comprising the steps of:

providing a catheter and needle assembly which includes;
a catheter having a body defining an interior passageway with a distal and a proximal opening,
a solid needle having a shaft and a distal tip,
a needle tip enclosure at said proximal opening, said enclosure containing a cavity therethrough, wherein at least a portion of said enclosure is transparent for viewing into the cavity;
said needle shaft having a length sufficient to extend through the enclosure cavity and the catheter passageway so that said needle tip emerges at said distal opening when in a first configuration;
said passageway and needle being cooperatively structured to provide a flow channel in said passageway for bodily fluids when in said first configuration;
said needle being of a size which permits it to be withdrawn from the catheter such that said needle tip can enter said cavity through a distal orifice of the enclosure, said needle tip being shaped to prevent egress of the needle tip from said cavity through a proximal orifice of the enclosure, and said enclosure, upon passage of said needle tip into the cavity through the distal orifice, prevents reemergence of said needle tip through the distal orifice;
wherein said catheter and needle assembly is in a second configuration when said needle tip is withdrawn from the catheter into said enclosure and is prevented from reemergence;
disposing said catheter and needle assembly in said first configuration and inserting said catheter and needle assembly into a patient;
inspecting said transparent portion of the housing for the presence of blood in the enclosure cavity;
shifting said catheter and needle assembly, after determining blood is present in the enclosure cavity, from said first configuration into said second configuration.

20. The method according to claim 19 including the additional step of:
detaching the needle and the enclosure with enclosed needle tip from the catheter, which is left inserted.

21. A method of inserting a catheter and needle assembly comprising the steps of:

providing a catheter and needle assembly which includes;
a catheter, a solid needle having a shaft and a needle tip, and a needle tip enclosure;
said catheter forming a hollow conduit with a distal opening, a proximal opening, and an aperture, said openings and aperture in fluid communication with an open volume within said conduit, said aperture in the vicinity of said distal opening, said open volume extending continuously between said openings;
said needle sized to slide within said conduit so that said shaft extends through but does not obstruct said conduit open volume and said needle tip emerges from and forms a seal with said distal opening when said catheter and needle assembly is in a first configuration;
said enclosure containing a cavity and having a distal orifice, a proximal orifice, and a transparent window providing visual inspection of said cavity, said distal orifice sized to allow passage of said needle shaft and said needle tip and said proximal orifice sized to allow passage of said needle shaft but not of said needle tip;
disposing said catheter and needle assembly in said first configuration wherein,
said enclosure distal orifice is joined to said catheter proximal opening so that said catheter open volume and said enclosure cavity are in fluid communication; and
said needle shaft passes through said catheter open volume and said enclosure cavity without obstruction of continuous fluid communication therethrough; and then
inserting said catheter and needle assembly sufficiently far into a blood vessel of a patient so that blood enters said catheter open volume through said aperture;
inspecting said cavity for blood entering from said catheter open volume; and
confirming correct insertion of said catheter by viewing the presence of blood within said cavity.

22. The method according to claim 21 wherein said enclosure further includes a needle tip retaining device for preventing reemergence of said needle tip after said needle tip enters into said enclosure cavity.

23. The method according to claim 22 including, upon confirming said catheter is correctly inserted, the additional steps of:
withdrawing said needle through said catheter and said enclosure until said needle tip enters and is retained within said enclosure; and
detaching said needle and enclosure with retained needle tip from the catheter, which is left inserted.

24. The method as set forth in claim 23 wherein the enclosure is moved distally simultaneous with proximal movement of the needle.

25. The method as set forth in claim 23 wherein movement of the needle with respect to the enclosure includes a wiping action, thereby cleaning the needle as it is withdrawn.

26. A method of inserting a catheter and needle assembly comprising the steps of:

providing a catheter and needle assembly which includes;
a catheter, a solid needle having a needle tip, and an enclosure;
said catheter having an aperture formed in the vicinity of its distal end, said aperture in fluid communication with an open volume within said catheter;
said enclosure at a proximal end of said catheter, said enclosure containing a cavity in fluid communication with said open volume within said catheter, said enclosure being at least partially transparent for viewing said cavity;

inserting said catheter and needle assembly sufficiently far into a blood vessel of a patient so that blood enters said catheter open volume through said aperture;

viewing said cavity for blood entering said cavity from said catheter open volume; and confirming correct insertion of said catheter by viewing blood within said cavity.

27. A catheter and needle assembly comprising:

a catheter having a body defining an interior passageway with a distal and a proximal opening, a needle having a shaft and a distal tip, a flash chamber in fluid communication with the interior passageway of the catheter, said needle and flash chamber being relatively movable with respect to each other;

said needle shaft having a length sufficient to extend through the flash chamber and the catheter passageway so that said needle tip emerges at the catheter distal opening, said passageway and needle providing a flow channel for bodily fluids to the flash chamber; and said needle being of a size which permits it to be withdrawn from the catheter.

28. The catheter and needle assembly of claim 27 wherein at least a portion of the flash chamber is transparent.

29. The catheter and needle assembly of claim 27 wherein appearance of bodily fluids in the flash chamber occurs upon placement of the distal end of the catheter in a vein of a human body.

30. The catheter and needle assembly of claim 27 wherein the needle and flash chamber are configured to minimize the total body fluid volume in the flash chamber.

31. The catheter and needle assembly of claim 27 wherein the flash chamber is movable distally away from a user of the assembly after the needle is inserted in a blood vessel of a human body so as to position blood contained in the flash chamber away from the hand of a user holding the proximal portion of the catheter and needle assembly.

32. A catheter and needle assembly comprising:

a catheter having a body defining an interior passageway with a distal and a proximal opening, a solid needle having a shaft and a distal tip, said needle shaft having a length sufficient to extend through the catheter passageway so that said needle tip emerges at the catheter distal opening, said passageway and needle being cooperatively structured to provide a flow channel in the catheter passageway for bodily fluids; and said needle being of a size which permits it to be withdrawn from the catheter, said catheter body having an aperture proximate the distal opening for entry of bodily fluids to the interior passageway.

\* \* \* \* \*